(12) United States Patent
Smith et al.

(10) Patent No.: US 7,157,446 B2
(45) Date of Patent: Jan. 2, 2007

(54) COMPLEX OF RAS-FARNESYLTRANSFERASE INHIBITOR, A CYCLODEXTRIN, AND ETHANOL

(75) Inventors: Anne Marie Smith, Glen Gardner, NJ (US); Michael Cucolo, Basking Ridge, NJ (US); Munir N. Nassar, Skillman, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 132 days.

(21) Appl. No.: 10/827,952

(22) Filed: Apr. 20, 2004

(65) Prior Publication Data

US 2004/0235790 A1 Nov. 25, 2004

Related U.S. Application Data

(60) Provisional application No. 60/467,287, filed on May 2, 2003.

(51) Int. Cl.
*A61K 31/724* (2006.01)
*A61K 31/715* (2006.01)

(52) U.S. Cl. .................. 514/58; 514/54; 514/221; 514/970; 514/973; 536/103

(58) Field of Classification Search .............. 514/58, 514/221, 970, 973, 54; 518/54; 536/103
See application file for complete search history.

(56) References Cited

U.S. PATENT DOCUMENTS

| | | | |
|---|---|---|---|
| 4,371,673 A | 2/1983 | Pitha | |
| 4,596,795 A | 6/1986 | Pitha | |
| 4,727,064 A | 2/1988 | Pitha | |
| 5,024,998 A | 6/1991 | Bodor | |
| 5,134,127 A | 7/1992 | Stella et al. | |
| 5,376,645 A | 12/1994 | Stella et al. | |
| 5,602,112 A | 2/1997 | Rubinfeld | |
| 5,646,131 A | 7/1997 | Badwan et al. | |
| 5,804,568 A | 9/1998 | Rubinfeld | |
| 5,855,916 A | 1/1999 | Chiesi et al. | |
| 6,011,029 A | 1/2000 | Ding et al. | |
| 6,048,845 A | 4/2000 | Rubinfeld | |
| 6,218,374 B1 | 4/2001 | Rubinfeld | |
| 6,218,375 B1 * | 4/2001 | Raghavan et al. | 514/58 |
| 6,407,079 B1 | 6/2002 | Müller et al. | |
| 6,455,523 B1 | 9/2002 | Ding et al. | |

FOREIGN PATENT DOCUMENTS

| | | |
|---|---|---|
| GB | 1193197 | 5/1970 |
| WO | WO 95/06485 | 3/1995 |

OTHER PUBLICATIONS

Saenger, "Cyclodextrin Inclusion Compounds in Research and Industry", Angew. Chem. Int. Ed. Engl., 19, pp. 344-362 (1980).
Okimoto et al., Pharmaceutical Research, 13, pp. 256-264 (1996).
Tinwalla et al., Pharmaceutical Research, 10, pp. 1136-1143 (1993).
Szejtli, "Cyclodextrins in Drug Formulations: Part I", Pharmaceutical Technology, pp. 36-44, Jun. 1991.
Rajewski et al., Journal of Pharmaceutical Sciences, 85 (11), pp. 1142-1168 (1996).
Chemical Abstracts 127:278213, "Imidazole-containing benzodiazepines and analogs as inhibitors of farnesyl protein transferase".
Brewster et al., "Effect of various cyclodextrins on solution stability and dissolution rate of doxorubicin hydrochloride", International Journal of Pharmaceutics, vol. 79, pp. 289-299 (1992).
Fenyvesi et al., "Water-Soluble Cyclodextrin Polymers and Their Complexing Properties," First International Symposium of Cyclodextrins, Budapest, Hungary 1981. J. Szejti, Editor. D. Reidel Publishing Co., 1982. pp. 345-359.
Pitha, Josef et al., "Effects of ethanol on formation of inclusion complexes of hydroxypropylcyclodextrins with testosterone or with methyl orange", Int'l J. of Pharmaceutics, 80, pp. 243-251 (1992).
Reer, Olaf et al., "Investigation of the Influence of Cosolvents and Surfactants on the Complexation of Dexamethasone with Hydroxypropyl-β-Cyclodextrin by Use of a Simple Lattice design", Eur. J. Pharm. Biopharm., 39 (3), pp. 105-111 (1993).
"Data Sheet: Hydroxypropyl B Cyclodextrin, Endotoxin Controlled", at http://www.researchd.com/janssen/410200.htm, pp. 1-13 (last visited Aug. 4, 2005).

* cited by examiner

*Primary Examiner*—Shaojia Anna Jiang
*Assistant Examiner*—Michael C. Henry
(74) *Attorney, Agent, or Firm*—Jacqueline M. Cohen; Maureen Gibbons

(57) ABSTRACT

A ras-farnesyltransferase inhibitor complex formed from a ras-farnesyltransferase inhibitor or a pharmaceutically acceptable salt thereof, a substituted cyclodextrin, and ethanol is provided. The complex has unexpectedly high aqueous solubility of the ras-farnesyltransferase inhibitor, improved dissolution, enhanced stability and is essentially free of particulate matter.

24 Claims, No Drawings

COMPLEX OF RAS-FARNESYLTRANSFERASE INHIBITOR, A CYCLODEXTRIN, AND ETHANOL

RELATED APPLICATIONS

This application claims priority benefit under Title 35 § 119(e) of U.S. Provisional Application No. 60/467,287, filed May 2, 2003, the contents of which are herein incorporated by reference.

FIELD OF THE INVENTION

The present invention relates to a ras-farnesyltransferase inhibitor complex that is essentially free of particulate matter, having improved water-solubility, and stability. The complex is useful as an anti-tumor agent.

BACKGROUND OF THE INVENTION

Cyclodextrins are cyclic oligosaccharides obtained from starch, formed of six glucose units (α-cyclodextrin), seven glucose units (β-cyclodextrin) or eight glucose units (γ-cyclodextrin). They are known to form inclusion compounds with smaller molecules which fit entirely or at least partially into the 5–8 Å cyclodextrin cavity, Saenger, W., "Cyclodextrin Inclusion Compounds in Research and Industry," Angew. Chem. Int. Ed. Engl. 19, 344–362 (1980). α-cyclodextrin forms complexes with water, methanol, polyiodide, iodine, krypton, n-propanol, p-iodoaniline, dimethyl sulfoxide, methanol, m-nitrophenol, methyl orange, prostaglandin E, and potassium acetate; β-cyclodextrin forms complexes with water, n-propanol, p-iodophenol, 2,5-diiodobenzoic acid, and p-nitroacetanilide; and γ-cyclodextrin forms complexes with propanol/water and water. β-cyclodextrin is also known to increase stabilization of benzocaine, procaine, atropine, aspirin, nitroglycerin, allicin, phenylbutazone, salicyclic acid, ascaridole, the ether ester of chaulmoogric acid, linoleic acid and indomethacin. However, β-cyclodextrin has nephrotoxicity and membrane destabilizing properties. Because of the safety concerns with β-cyclodextrins, numerous chemical modifications of the cyclodextrins have been made. The different types of β-cyclodextrins are alkylated cyclodextrins, hydroxyalkylated cyclodextrins, carboxymethyl cyclodextrins and the sulfoalkylether cyclodextrins which include sulfobutylether (SBE) β-cyclodextrins, with degrees of substitution on 4 and 7 positions of β-cyclodextrin. The specific product in the last group includes Captisol®, an SBE 7-β-cyclodextrin (SBE-CD).

U.S. Pat. No. 4,596,795 discloses the administration of sex hormones, particularly testosterone, progesterone and estradiol in the form of their complexes or inclusions with specific derivatives of cyclodextrins by the sublingual or buccal route resulting in effective transfer of these hormones into the systemic circulation, followed by only gradual elimination.

U.S. Pat. No. 4,727,064 is directed to the method of conversion of drug compositions which themselves are crystalline and of low water-solubility into intrinsically amorphous complexes which have improved pharmaceutical properties. This conversion is achieved by inclusion of the above drug compositions into water-soluble, multi-component mixtures of cyclodextrin derivatives.

U.S. Pat. Nos. 5,134,127 and 5,376,645 disclose sulfoalkyl ether cyclodextrin derivatives and their use as solubilizing agents for water-insoluble drugs for oral, intranasal or parenteral administration.

U.S. Pat. No. 5,602,112 discloses pharmaceutical formulations containing an antiulcerative amount of a substituted cyclodextrin, an inherently water-soluble cytotoxic anticancer drug, and a sugar alcohol, such as mannitol. The cyclodextrin derivatives taught by this disclosure are used to ameliorate the ulcerative effects of the drugs and not to increase water-solubility because the drugs are inherently water-soluble. The sugar alcohol is added to enhance the ameliorative effect of the substituted cyclodextrin on the extravasation toxicity (ulceration) of the cytotoxic agents.

U.S. Pat. No. 6,218,375 discloses a ras-farnesyltransferase inhibitor complex comprising a compound having the formula I:

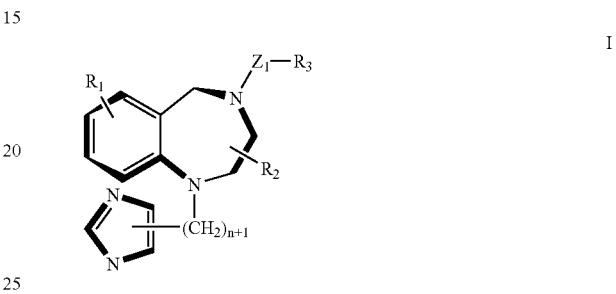

in combination with substituted cyclodextrins such as sulfobutylether-7-β-cyclodextrin and 2-hydroxypropyl-β-cyclodextrin. Although this complex has been found to be useful for treating cancer, there is a need in the art for FTI formulations having improved solubility, stability, and dissolution profiles that are suitable for parenteral use.

SUMMARY OF THE INVENTION

The present invention is directed to a ras-farnesyltransferase inhibitor (FTI) complex comprising an inhibitor having formula I, or a pharmaceutically acceptable salt thereof:

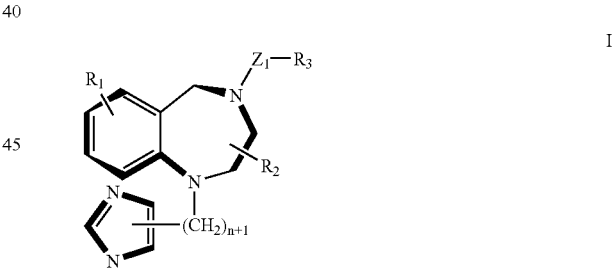

wherein n is 0 or 1; $R_1$ is selected from Cl, Br, phenyl, pyridyl or cyano; $R_2$ is aralkyl; $R_3$ is selected from lower alkyl, aryl or substituted aryl or heterocyclo; $Z_1$ is selected from CO, $SO_2$, $CO_2$, or $SO_2NR_5$, $R_5$ is selected from hydrogen, lower alkyl or substituted alkyl; from about 10% w/v to about 40% w/v ethanol, and a sulfobutylether-7-β-cyclodextrin or a 2.

In some embodiments of the present invention, ethanol is present in an amount ranging from about 15% to about 35%.

In some embodiments of the present invention, ethanol is present in an amount ranging from about 20% to about 30%.

In some embodiments of the present invention, ethanol is present in an amount ranging from about 25% to about 30%.

In a preferred embodiment of the present invention, ethanol is present in an amount of about 30%.

Also disclosed are pharmaceutical compositions comprising an effective amount of a ras farnesyl transferase inhibitor, a substituted cyclodextrin, such as those discussed above, and from about 10% w/v to about 40% w/v ethanol, in a pharmaceutically acceptable carrier.

DETAILED DESCRIPTION

The present invention provides pharmaceutical formulations or complexes comprising a ras-farnesyltransferase inhibitor of formula I, or a pharmaceutically acceptable salt thereof:

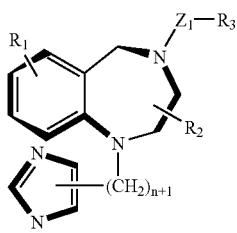

I wherein n is 0 or 1; $R_1$ is Cl, Br, phenyl, pyridyl or cyano; $R_2$ is aralkyl; $R_3$ is lower alkyl, aryl, substituted aryl or heterocyclo; $Z_1$ is CO, $SO_2$, $CO_2$, $SO_2NR_5$ wherein $R_5$ is hydrogen, lower alkyl or substituted alkyl; a substituted cyclodextrin, such as sulfobutylether-7-β-cyclodextrin or a 2-hydroxypropyl-β-cyclodextrin; and from about 10% w/v to about 40% w/v ethanol. Formulations of the present invention have markedly improved water-solubility and stability and also exhibit faster dissolution profiles than those of the prior art. Additionally, the formulations are essentially free of particulate matter as required by the compendial specifications for injectables in the USP 26-NF 21, herein incorporated by reference in its entirety.

Definitions

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONH alkyl, CONH aryl, CONH aralkyl or cases where there are two substituents on the nitrogen selected from alkyl, aryl or aralkyl; alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl, substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "heterocyclo" refers to an optionally substituted, fully saturated or unsaturated, aromatic or non aromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. The heterocyclo groups may also be substituted with any of the substituents described herein regarding alkyl or aryl groups.

The term "cyclodextrin" includes sulfobutylether-7-β-cyclodextrin and 2-hydroxypropyl-β-cyclodextrin.

Ethanol percentages are expressed in terms of w/v.

The FT inhibitors of formula I may form salts with a variety of organic and inorganic acids. Such salts include those formed with hydrogen chloride, hydroxymethane sulfonic acid, hydrogen bromide, methanesulfonic acid (MSA), sulfuric acid, acetic acid, trifluoroacetic acid, maleic acid, benzenesulfonic acid, toluenesulfonic acid and various others e.g., nitrates, phosphates, borates, tartrates, citrates, succinates, benzoates, ascorbates, salicylates and the like. Such salts may be formed by reacting a formula I inhibitor in an equivalent amount of the acid in a medium in which the salt precipitates or in an aqueous medium followed by evaporation. The pharmaceutically and physiologically acceptable non-toxic salts are preferred, although other salts are also useful, e.g., in isolating or purifying the formula I inhibitors of the present invention or salt forms thereof.

Preferred FT inhibitors of the present invention include,
(R)-7-cyano-2,3,4,5-tetrahydro-1-(1H-imidazol-4-ylmethyl)-3-(phenylmethyl)-4-(2-thienylsulfonyl)-1H-1,4-benzodiazepine, or its salt;
(R)-2,3,4,5-tetrahydro-1-(1H-imidazol-4-ylmethyl)-4-phenylsulfonyl)-3-(phenylmethyl)-1H-1,4-benzodiazepine-7-carbonitrile, or its salt;
(R)-7-bromo-2,3,4,5-tetrahydro-1-(1H-imidazol-4-ylmethyl)-4-(methylsulfonyl)-3-(phenylmethyl)-1H-1,4-benzdiazepine, or its salt;
(R)-7-cyano-2,3,4,5-tetrahydro-1-1H-imidazol-4-ylmethyl)-3-(phenylmethyl)-4-(propylsulfonyl)-1H-1,4-benzodiazepine, or its salt; and
(R)-7-cyano-4-[(4-fluorophenyl)sulfonyl]-2,3,4,5-tetrahydro-1-(1H-imidazol-4-ylmethyl)-3-(phenylmethyl)-1H-1,4-benzodiazepine, or its salt.

These and additional FT inhibitors that are useful in the present invention, and methods for making them, are described in U.S. Pat. No. 6,011,029, herein incorporated by reference in its entirety.

In general, the complex of the invention comprises the FTI and the cyclodextrin in a molar ratio of about 1:2 or higher in a solution of ethanol and water. The complex may be formed by preparing an aqueous solution of cyclodextrin and ethanol and adding the freebase or a salt of the ras-farnesyltransferase inhibitor to it with stirring and adjusting the pH with an appropriate acid or well-known aqueous buffer to the desired pH value.

According to one embodiment of the present invention, the complex is formed by preparing an aqueous, pH 4 buffer solution containing 0.155 grams citric acid and 0.076 grams sodium citrate. While mixing, 10 grams of sulfobutylether-7-β-cyclodextrin is added to 70 milliliters of the buffered solution followed by the addition of 30 grams of ethanol and mixed. To this solution is added 1 gram of the ras-farnesyltransferase inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine (hereinafter referred to as "compound I") and after the addition of the inhibitor, the solution is additionally mixed for thirty minutes at room temperature. The solution is then filtered using a 0.22 micron filter.

Formulations of the present invention have improved water-solubility and stability and faster dissolution profiles than those of the prior art. For example, the aqueous solubility of the inhibitor (R)-7-cyano-2,3,4,5-tetrahydro-1-(1H-imidazol-4-ylmethyl)-3-(phenylmethyl)-4-(2-thienylsulfonyl)-1H-1,4-benzodiazepine is surprisingly increased in the presence of sulfobutylether-7-β-cyclodextrin and ethanol. The solubility of this inhibitor as the MSA salt increased from 1.7 mg/mL in water, to 13 mg/mL in 10% w/v SBE-CD. The solubility increased to 14 mg/mL in 10% w/v SBE-CD and 25% ethanol w/v, to 20 mg/mL in 10% w/v SBE-CD and 30% w/v alcohol and further still to 28 mg/mL in 10% w/v SBE-CD and 40% w/v alcohol. Thus, depending on the concentration of ethanol in the solution with 10% w/v SBE-CD, the aqueous solubility of this inhibitor is found to increase by greater than 50% (i.e. from 13 mg/mL with no ethanol to 28 mg/ml with 40% ethanol).

The enhanced solubility and stability of the preferred complex, its dilutability profile and the absence of particulates, makes this formulation suitable over other possible formulations for parenteral administration. For example, FTI complexes containing SBE-CD and compounds having formula I with additives such as Tween 80, PEG, PVP, or Cremophor do not have all of the preferred properties of the present invention.

The present invention also provides pharmaceutical compositions comprising the ras-farnesyltransferase inhibitor of formula I with a substituted cyclodextrin, such as sulfobutylether-7-β-cyclodextrin, and ethanol together with a pharmaceutically acceptable carrier and optionally other therapeutic and prophylactic ingredients. The carrier ingredients for the pharmaceutical formulation may include, as appropriate, diluents, buffers, flavoring agents, binders, thickeners, lubricants, preservatives and the like. The carriers must be acceptable in the sense of being compatible with the other ingredients of the formula and not deleterious to recipient thereof.

The preferred mode of administration of the complex of the present invention is parenteral, which includes subcutaneous injections, intravenous, intramuscular, intrastemal injection or infusion techniques. In addition to the treatment of warm-blooded animals such as mice, rats, dogs, cats, etc., the complex of the invention is effective in the treatment of humans with cancer.

The following examples represent preferred embodiments of the present invention and are not intended to limit the scope of the present invention.

EXAMPLES

All temperatures are expressed in degrees Centigrade unless otherwise indicated. Sulfobutylether-7-β-cyclodextrin (SBE-CD) is commercially available from CyDex™ under the tradename Captisol®.

Example 1

Preparation of a 250 mL Complex of SBE-CD, Ethanol and MSA Salt of Compound I in an Unbuffered System 140 mL of Water for Injection was added to a beaker. With stirring, at room temperature, 25.0 grams of Captisol® was added and dissolved. With continued stirring, 75.0 grams of ethanol was added. With continued mixing 2.97 grams of compound I was added to the solution and the mixture stirred for an additional 30 minutes at room temperature to completely dissolve the compound I. The pH of the resulting solution is between 4.0 and 4.3. The volume of the solution was adjusted to 250 mL with Water for Injection. The solution was thoroughly mixed and filtered through a 0.22 um filter. The clear filtrate contained the complex of 10 mg/mL of compound I in 10% w/v SBE-CD and 30% w/v ethanol.

Example 2

Preparation of a 100 mL Complex of SBE-CD, Ethanol and MSA Salt of Compound I in 10 mMol Citric Acid Buffer 50 mL of Water for Injection was added to a beaker. With stirring, at room temperature, 0.155 grams of citric acid and 0.076 grams of sodium citrate was added. With continuous stirring, 10.0 grams of Captisol® was added and dissolved. With continuous stirring 30.0 grams of ethanol was added. While stirring, 1.19 grams of compound I (as the MSA salt) was added to the solution and the mixture stirred for an additional 30 minutes at room temperature. The pH of the resulting solution is 4.0. After that the volume of the solution was adjusted to 100 mL with Water for Injection. The solution was thoroughly mixed and filtered through a 0.22 um filter. The clear filtrate contained the complex of 10 mg/mL of compound I in 10% w/v SBE-CD and 30% w/v ethanol in a 10 mM citric acid buffer.

Example 3

Preparation of a 500 mL Complex of SBE-CD, Ethanol, and MSA Salt of Compound I in 10 mMol Citric Acid Buffer 250 mL of Water for Injection was added to a beaker. With stirring, at room temperature, 0.775 grams of citric acid monohydrate and 0.380 grams of sodium citrate dihydrate was added. With continued stirring, 50.0 grams of Captisol® was added and dissolved. With continued stirring, 150.0 grams of dehydrated alcohol was added. With continued stirring, 5.94 grams of compound I (as the MSA salt) was added to the solution and the mixture stirred for an additional 30 minutes, at room temperature, until compound I was completely dissolved. The pH of the resulting solution is between 4.0 and 4.3. The volume of the solution was adjusted to 500 mL with Water for Injection. The solution was thoroughly mixed then filtered through a 0.22 μm filter. The clear, colorless filtrate contains the complex of 10 mg/mL of compound I in 10% w/v SBE-CD and 30% w/v/ethanol in a 10 mM citric acid buffer.

What is claimed is:

1. A ras-farnesyltransferase inhibitor complex comprising an inhibitor having formula I, or a pharmaceutically acceptable salt thereof:

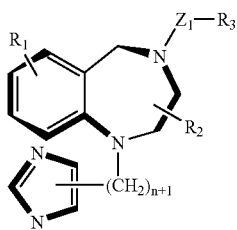

I wherein
  n is 0 or 1;
  $R_1$ is selected from Cl, Br, phenyl, pyridyl or cyano;
  $R_2$ is aralkyl;
  $R_3$ is selected from lower alkyl, aryl or substituted aryl or heterocyclo;
  $Z_1$ is selected from CO, $SO_2$, $CO_2$, or $SO_2NR_5$, $R_5$ is selected from hydrogen, lower alkyl or substituted alkyl; and
  sulfobutylether-7-β-cyclodextrin or 2-hydroxypropyl-β-cyclodextrin in a molar ratio of the inhibitor to cyclodextrin within the range of from about 1 to 2 or higher; and
  from about 10% w/v to about 40% w/v ethanol.

2. The complex of claim 1, wherein said cyclodextrin is sulfobutylether-7-β-cyclodextrin.

3. The complex of claim 2, wherein the inhibitor is (R)-7-cyano-2,3,4,5-tetrahydro-1-(1H-imidazol-4-ylmethyl)-3-(phenylmethyl)-4-(2-thienylsulfonyl)-1H-1,4-benzodiazepine or a pharmaceutically acceptable salt thereof.

4. The complex of claim 3 wherein said ethanol is present in an amount ranging from about 15% to about 35%.

5. The complex of claim 3 wherein said ethanol is present in an amount ranging from about 20% to about 30%.

6. The complex of claim 3 wherein said ethanol is present in an amount ranging from about 25% to about 30%.

7. The complex of claim 2 wherein said ethanol is present in an amount of about 30%.

8. A ras-farnesyltransferase inhibitor composition, comprising an effective amount of the complex of claim 1 and a pharmaceutically acceptable carrier.

9. The composition of claim 8, wherein said composition is in liquid form.

10. The composition of claim 8, wherein the carrier is citric acid buffer.

11. The composition of claim 8, which further comprises diluents of electrolytes or nonelectrolytes.

12. A ras farnesyltransferase inhibitor complex comprising a (R)-7-cyano-2,3,4,5-tetrahydro-1-(1H-imidazol-4-yl-methyl)-3-(phenylmethyl)-4-(2-thienylsulfonyl)-1H-1,4-benzodiazepine or a pharmaceutically acceptable salt thereof as inhibitor and sulfobutylether-7-β-cyclodextrin in a molar ratio of the inhibitor to sulfobutylether-7-β-cyclodextrin within the range of from about 1 to 2 and from about 10% w/v to about 40% w/v ethanol.

13. The complex of claim 12, wherein said ethanol is present in an amount ranging from about 20% to about 30%.

14. The complex of claim 12, wherein said ethanol is present in an amount of about 30% ethanol.

15. A method of treating a tumor susceptible to farnesyl transferase inhibition comprising administering to a patient in need thereof an effective amount of the complex of claim 1.

16. The method according to claim 15, wherein the complex of claim 1 is administered parenterally.

17. The complex of claim 1, wherein said ethanol is present in an amount ranging from about 15% to about 35%.

18. The complex of claim 1, wherein said ethanol is present in an amount ranging from about 20% to about 30%.

19. The complex of claim 1, wherein said ethanol is present in an amount ranging from about 25% to about 30%.

20. The complex of claim 1, wherein said ethanol is present in an amount of about 30%.

21. The composition of claim 9, wherein said composition is essentially free of particulate matter.

22. The complex of claim 1, wherein said complex is essentially free of particulate matter.

23. The complex of claim 12, wherein said complex is essentially free of particulate matter.

24. A ras farnesyltransferase inhibitor complex comprising about 1.19% w/v (R)-7-cyano-2,3,4,5-tetrahydro-1-(1H-imidazol-4-ylmethyl)- 3-(phenylmethyl)-4-(2-thienylsulfonyl)-1H-1,4-benzodiazepine or a pharmaceutically acceptable salt thereof, about 10% w/v sulfobutylether-7-β-cyclodextrin, and about 30% w/v ethanol.

* * * * *